United States Patent [19]
Okubo et al.

[11] Patent Number: 5,366,725
[45] Date of Patent: Nov. 22, 1994

[54] METHOD FOR THE TREATMENT OF CANCER

[76] Inventors: Shinya Okubo, 6-1, Noboricho 2 chome; Mitsunobu Sato, 187-10, Shimofukuman, Hachiman-cho; Kunisuke Himeno, 188-18, Shimofukman, Hachiman-cho, all of, Tokushima-shi, Tokushima 770, Japan

[21] Appl. No.: 48,206

[22] Filed: Apr. 20, 1993

Related U.S. Application Data

[62] Division of Ser. No. 834,309, Feb. 26, 1992, abandoned.

[30] Foreign Application Priority Data

Jun. 27, 1990 [JP] Japan .................... 2-171978

[51] Int. Cl.5 .................... A61K 35/78; A61K 35/12; A61K 37/04
[52] U.S. Cl. .................... 424/85.4; 424/85.7; 514/23
[58] Field of Search .................. 514/23; 424/85.4, 85.7

[56] References Cited
PUBLICATIONS

Rosenberg et al., "observations on the Systemic Administration . . . with Metastatic Cancer," 313 New England J. Med. 1485 (1985).
Clark et al., "Interleukin −2 and Lymphokine-Activated . . . Interleukin-2 Regimen," 50 Cancer Reseach 7343, 7347 (1990).
Rosenberg et al., "A Progress Report . . . High Dose Il-2 Alone," 316 New England J. Med. 889 (1987).
West et al., "Constant Infusion Recombinant . . . Adanced Cancer," 316 New England J. Med. 898 (1987).
Rosenberg et al., "A Progress Report . . . High Dose Interleukin 2 Alone," 316 New England J. Med. 889 (1987).
West et al., "Constant Infusion Recombinant . . . Advanced Cancer," 316 New England J. Med. 898 (1987).
Weiner et al., "Phase I Evaluation . . . Interleukin–Z and Y Interferon," 51 Cancer Research 3901 (1991).
Rosenberg et al., "Observations on the Systemic Administration . . . With Metastatic Cancer", 313 New England Journal Med. 1485 (1985).
Clark et al., "Interleukin 2 and Lymphokine-activated . . . Interleukin 2 Regimen," 50 Cancer Research 7343, 7347 (1990).
Weiner et al., "Phase I Evaluation . . . and Y Interferon," 51 Cancer Research 3901 (1991).
Japanese Patent Publication 2-83331 (Okubo et al) Published Mar. 23, 1990 with English language Summary.

*Primary Examiner*—Lester L. Lee
*Assistant Examiner*—Pihyun Touzeau
*Attorney, Agent, or Firm*—Armstrong, Westerman, Hattori, McLeland & Naughton

[57] ABSTRACT

The carcinostatic agent of the present invention is an extract from seeds of *Aeginetia indica* and has interleukin-2 and interferon-γ inducing potency. As shown in FIG. 1, all of the mice, to which this extract was not given, (Δ) died from tumor (6 mice). In contrast, in the mice, to which the extract was given by 0.6 mg/kg (□), 1.2 mg/kg (+), and 2.5 mg/kg (◊) intraperitoneally once in every two days from the day of tumor grafting, all mice showed increase in the survival rate. Thus, the extract exhibits excellent carcinostatic effect.

3 Claims, 10 Drawing Sheets

METHOD FOR THE TREATMENT OF CANCER

This application is a division of application Ser. No. 07/834,309 filed Feb. 26, 1992, now abandoned.

FIELD OF THE INVENTION

The present invention relates to a carcinostatic agent, which is an extract having a potency to induce interleukin-2 and interferon-γ extracted from seeds of *Aeginetia indica*.

TECHNICAL BACKGROUND

An interleukin or interferon inducing agent is a substance to induce interleukin (IL) or interferon (IFN) by exerting action on human or animal cells. A wide variety of natural substances are known to have such action. For example, a Chinese herb medicine "Tohki" is processed with hot water, and a substance having IFN inducing activity is isolated from the extract (Japanese Provisional Patent Publication No. 53-32107), or another substance having IFN inducing activity is isolated from a Chinese herb medicine "Souhakuhi" (Japanese Provisional Patent Publication No. 53-99313).

Broomrape (*Aeginetia indica* L; AIL) has been known as a roborant and is an annual non-chlorophyllous plant of broomrape family, *Aeginetia indica* genus. It lives on roots of such plants as eulalia, Japanese ginger, sugar cane, etc., and its fruit contains innumerable fine seeds similar to dust ("General Medicinal Plants", Hirokawa Publishing Co., 1936; pp. 106–107).

The present inventors have found that a substance extracted from the seeds of *Aeginetia indica* contains a component having prominent IL-2 and IFN-γ inducing activity but giving no side effect. It is an object of the present invention to provide a carcinostatic agent containing an extract from the seeds of *Aeginetia indica*.

DISCLOSURE OF THE INVENTION

The carcinostatic agent according to the present invention is characterized in that it is extracted from seeds of *Aeginetia indica* and has a potency to induce interleukin-2 and interferon-γ.

This substance to induce interleukin-2 and interferon-γ is obtained from seeds of *Aeginetia indica* as follows:

(1) It is extracted with distilled water, and in particular, with distilled water with phosphate buffer physiological saline; or (2) it is extracted from seeds of *Aeginetia indica* with water-saturated butanol, and water layer thus obtained is processed with pronase, and the substance is collected by ultrafiltration of the solution after the precipitate has been removed; or (3) the substance is extracted from seeds of *Aeginetia indica* with water-saturated phenol. The water layer thus obtained is processed with potassium acetate and ethanol. After removing the precipitate, the solution is dialyzed against distilled water. After removing RNA from the dialyzed solution, the water layer obtained is further processed with potassium acetate and ethanol. After removing the precipitate, the solution is dialyzed against distilled water, and the substance is obtained by condensing the dialyzed solution.

BEST MODE FOR CARRYING OUT THE INVENTION

First, concrete description will be given on a method to extract a substance having a potency to induce interleukin-2 and interferon-γ from seeds of *Aeginetia indica*.

Extraction Example 1

Preparation of an extract from seeds of *Aeginetia indica* with phosphate buffer physiological saline (hereinafter referred as "crude extract")

To 40 mg of seeds of *Aeginetia indica*, 1 ml of 0.1M phosphate buffer physiological saline (pH 7.2) not containing calcium and magnesium ions was added, and the mixture was pulverized in a mortar. The pulverized mixture was centrifuged at 15,000 g and 4° C. for 15 minutes, and the supernatant was passed through Millipore filter of 0.45 μm in pore size and was sterilized. Thus, the extract of the present invention was obtained.

Extraction Example 2

To the pulverized seeds of *Aeginetia indica* as described above, water-saturated butanol of the same volume was added, and it was agitated at 0° C. for 15 minutes. The mixture was then centrifuged at 35,000 g for 20 minutes, and the separated lower water layer was collected. The butanol layer and the precipitate were extracted with butanol by two times, and the water layer fraction thus obtained was further centrifuged, and insoluble matters were removed. A protein decomposing enzyme, pronase, was added to have the final concentration of 20 μg/ml, and it was left at 37° C. overnight. By this processing with pronase, white precipitation of protein containing pronase occurred, and this precipitate was removed by centrifugation.

Next, the solution after removing the precipitate was condensed at a pressure of 1.5 kg/cm², using an ultrafiltration membrane (Amicon; U.S.A.) with cutoff molecular weight 3500 and core side 3000. Thus, the extract of the present invention was obtained. By determining uronic acid, the yield was measured as 45 mg per 1 g of seeds of *Aeginetia indica*.

Extraction Example 3

To the pulverized seeds of *Aeginetia indica* as described above, water-saturated phenol of the same volume was added and was agitated at 0° C. for 30 minutes. Then, it was centrifuged at 200 g for 10 minutes, and water layer was separated. Phenol mingled in the water layer was extracted with ether and was removed, and the ether dissolved in the water layer was removed by passing nitrogen gas. To the phenol extract thus obtained, potassium acetate was added by 2% (w/w), and 95% ethanol was added by 10 times as much as the volume of the solution. After leaving it at 4° C. overnight, the resultant precipitate was dissolved in distilled water.

To this solution, potassium acetate was added by the same ratio of 2%, and this was mixed with the same volume of ethanol, and it was left at 0° C. for 30 minutes. Then, it was centrifuged at 5,000 g for 20 minutes, and the precipitate primarily containing RNA was discarded. Further, ethanol of by 6 times in volume was added to the supernatant. After leaving it for one hour, the precipitate was centrifuged at 5,000 g for 20 minutes. This was dissolved in distilled water and was dialyzed against distilled water.

Because polysaccharides and trace quantity of RNA were mixed in this dialyzed solution, 30-40 μg of bovine pancreatic RNase was added per 1 ml for the purpose of destroying RNA, and it was left at 38° C. for one hour. After the processing, 2% potassium acetate and ethanol by 6 times in volume were added. The resultant precipitate was collected by centrifugation, was dissolved in distilled water and was centrifuged at 200 g. The supernatant obtained was dialyzed against distilled water, and the dialyzed solution was condensed and was used as the standard item in the extraction example 3. By determining uronic acid, the yield was measured as 38 mg per 1 g of seeds of *Aeginetia indica*.

As described above, the extracted substance according to the present invention is a macromolecular polysaccharide, which is extracted from the seeds of *Aeginetia indica* with distilled water, and in particular, with phosphate buffer physiological saline, or it is obtained by the method of Morrison et al. (Morrison & Leive. Fractions of Lipopolysaccharide from *Escherichia coli* 0111:B4 Prepared by Two Extraction Procedures.; J. Biol. Chem. 250; 2911-2919, 1975), or by a similar method by Westphal et al. (Westphal, O. and Luderitz, O., Chemische Erforschung von Lipopolyschariden grammnegativer Bakterien, Angew. Chem. 66; 407-417, 1954).

Very little is known above the structure and the composition of the polysaccharides in the extracted substance. When the seeds of *Aeginetia indica* is extracted with water-saturated phenol by the method of Westphal et al., polysaccharides not binding with protein almost at all are obtained. On the other hand, when it is extracted with water-saturated n-butanol using the method of Morrison et al., the saccharide containing lipid A binding with protein is extracted.

The extracted substance of the present invention is water-soluble and insoluble in n-butanol and does not contain RNA (measured by Mezbaum method using orcinol reaction and by UV absorption), and molecular weight is within the range of 100,000-200,000.

Next, description is given on the fact that the substance extracted from the seeds of *Aeginetia indica* as described above has a potency to induce interleukin-2 and interferon-γ.

First, the following chemical analysis was performed on polysaccharide fractions extracted from the above extraction examples.

Uronic acid was quantitatively analyzed by the method of Bitter et al. using carbazole reaction (Bitter, T. and Ewins, R.: A modified carbazole reaction for uronic acids.; Biochem. J. 81; 43, 1961), and RNA was determined by the method of Mezbaum using orcinol reaction {Mezbaum, W.: Color reactions of nucleic acid components; In The nucleic acids. (Chargaff, E., and Davidson, J., editors). Academic Press, New York. 1; 283-305, 1939 } and by UV absorption. Protein was quantitatively determined by the method of Follin et al. (Follin, O, and Clocalteau, V.: On tyrosine and tryptophane determination in proteins. J. Biol. Chem. 73; 627-650, 1927) and by UV absorption.

Examination of IL-2 and IFN-γ Activity

Preparation of the standard item for study

From heparinized human peripheral blood, peripheral blood mononuclear cells (hereinafter referred as "PBMC") were isolated by density-gradient centrifugation (density: 1.077; Boyum, A. Isolation of mononuclear cells and granulocytes from human blood; Scan. J. Clin. Invest. 21; 77-89, 1967), and $10^7$/ml of cell suspension was prepared using leukocyte proliferation culture solution (RPMI-1640), which contains 10% fetal bovine serum.

To 1 ml of this PBMC suspension, 1 ml each of fractions extracted in the above extraction examples was added, and this was incubated at 37° C. for 24 and 48 hours in the air containing 5% carbon dioxide. After the supernatant of this culture solution was centrifuged at 500 g for 15 minutes, it was passed through Millipore filter and sterilized to prepare the standard item, and this was used for examining IL-2 and IFN-γ activity study as described below.

IL-2 activity measuring method

Using CTLL cells with IL-2-dependent cell proliferation, $5 \times 10^3$ CTLL cells were suspended in 200μl of culture solution containing 10% standard item to be tested on 96-well microplate, and this was incubated at 37° C. for 24 hours in an incubator with 5% carbon dioxide. Then, 0.5 μCi each of $^3$H-thymidine (Amersham; U.K.) was added to each well, and this was further incubated for 16 hours. Then, the uptake of $^3$H-thymidine was measured by a liquid scintillation counter. In this case, the titer of IL-2 was calculated from the uptake of $^3$H-thymidine when CTLL cells were processed with the standard item, which had been prepared so that recombinant type IL-2 (Shionogi) will have final concentration of 5.0, 2.5, 1.25, 0.63 and 0.31 unit/ml. IFN-γ activity measuring method FL cells ($10^6$) derived from human amnion was inoculated to plastic Petri dish with diameter of 60 mm, and this was incubated in an incubator with 5% carbon dioxide at 37° C. for 2 days, and FL monolayer cells were prepared.

Next, 0.8 ml of minimum essential medium was added to 0.2 ml of the standard item to be tested, and FL monolayer cultured cells were processed with 0.5 ml of the solution of the standard item diluted by 5 times at 37° C. for 12 hours. Then, the plaque-forming potency of vesicular stomatitis virus (VSV) in the treated FL monolayer cultured cells was compared with the VSV plaque-forming potency of untreated FL monolayer cultured cells and calculated. IFN titer was expressed by maximum dilution ratio of the standard item required for decreasing VSV plaque-forming potency by 50%.

IFN typing method

For the typing of IFN contained in the standard item, 0.2 ml of anti-IFN-$\alpha/\beta$ antibody (National Institute of Health, U.S.A.) was added to 0.2 ml of the standard item, and 0.2 ml of anti-IFN-$\gamma$ antibody (Interferon; Sciences Inc., U.S.A.) was added to 0.2 ml of the standard item. After incubating at 37° C. for 30 minutes, 0.6 ml of minimum essential medium was added to make the total volume to 1 ml. Using 0.5 ml of this standard item, FL monolayer cultured cells were treated at 37° C. for 12 hours, and VSV plaque-decreasing ratio was measured by the above procedure. The anti-IFN-$\alpha/\beta$ antibody or the anti-IFN-$\gamma$ antibody was prepared in such manner that it has a titer to neutralize 100 units of IFN-$\alpha$ or IFN-$\beta$, or 100 units of IFN-$\gamma$.

Chromatography of the extract

The extract prepared in the extraction example 2 was eluted with 0.15M NaCl in 0.02M Tris-HCl buffer solution (pH 7.4), using column chromatography (Sephadex G-200, Pharmacia, Sweden; Column size: 0.9 cm (dia)$\times$30 cm), and 20 fractions were collected (2 ml in each fraction). $1\times10^7$/ml of PBMC were inoculated into each hole of 24-well plate and 0.1 ml of each fraction was added, and this was incubated at 37° C. for 24 hours. Then, the supernatant was collected, and IL-2 activity was measured.

Next, description is given on the method to measure IL-2 inducing potency of crude extraction standard item as extracted in the extraction example 1.

The crude extraction standard item as extracted in the extraction example 1 and PBMC were incubated for 24 and 48 hours, and the supernatant was measured by the above method to measure IL-2 titer.

Figure 8:
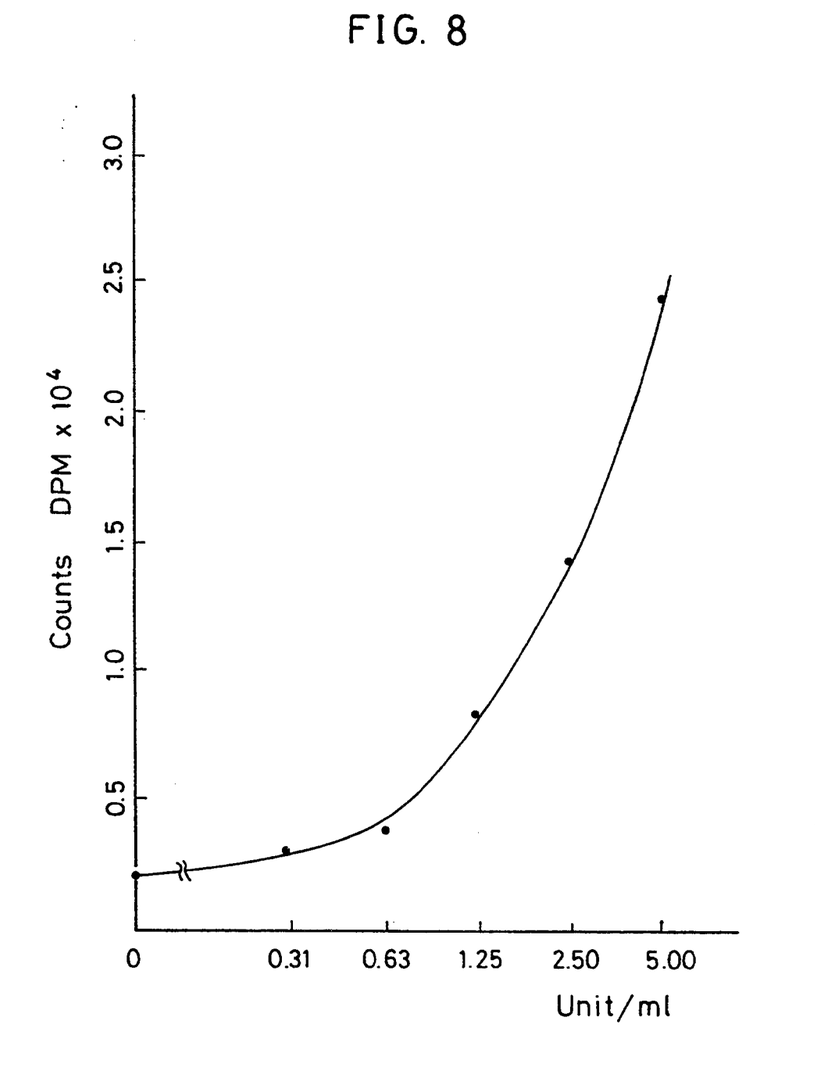
FIG. 8, FIG. 9 and FIG. 10 are diagrams to explain that an extract from seeds of *Aeginetia indica* has IL-2 and IFN inducing potency.

FIG. 8 shows a quantitative curve prepared from the standard IL-2 (recombinant IL-2), where the abscissa represents the standard IL-2 (unit/ml), and $^3$H-thymidine uptake is given on the ordinate. For the supernant of the culture solution prepared through incubation for 24 and 48 hours as described above, the counts showing $^3$H-thymidine uptake (unit in DPM) were measured, and IL-2 (unit/ml) corresponding to the counts was obtained from FIG. 8. The results are shown in Table 1.

TABLE 1

| Standard item | $^3$H-thymidine uptake | IL-2 titer (unit/ml) |
| --- | --- | --- |
| 24 hours | 54030 | 8 |
| 48 hours | 24790 | 2.2 |

As it is evident from Table 1, the crude extraction standard item of seeds of *Aeginetia indica* according to the present invention possesses IL-2 inducing potency.

Next, description is given on the method to measure IFN producing potency of crude extraction standard item of the seeds of *Aeginetia indica* prepared in the extraction example 1.

The crude extraction standard item of seeds of *Aeginetia indica* prepared in the extraction example 1 and PBMC were incubated for 24 or 48 hours, and the supernatant was diluted by 10 times. Using this, FL monolayer cultured cells were treated, and VSV plaque-forming potency was measured. The plaque decreasing ratio is calculated by the following formula. Table 2 summarizes the results of two experiments.

$$\left(1 - \frac{\text{Number of plaques in treated standard item}}{\text{Number of plaques in untreated control}}\right) \times 100$$

TABLE 2

|  | No. of plaques | Average | Decreasing ratio |
| --- | --- | --- | --- |
| Untreated | 78, 87 | 82.5 | — |
| 24 hours | 43, 35 | 39 | 52.4 |
| 48 hours | 51, 47 | 49 | 40.6 |
| Untreated | 112, 106 | 109 | — |
| 24 hours | 37, 41 | 39 | 74.2 |
| 48 hours | 67, 5 | 61.5 | 43.6 |

From Table 2, it is confirmed that the crude extraction standard item of seeds of *Aeginetia indica* possesses IFN producing potency. In particular, the 24-hour standard item has higher IFN activity than the 48-hour standard item.

Next, description is given on the typing method of IFN induced from the crude extraction standard item from seeds of *Aeginetia indica*.

PBMC was treated with the crude extraction standard item of the seeds of *Aeginetia indica* for 24 hours, and the supernatant was diluted by 5 times, and this was used in the experiment. The experiment was performed twice, and the results are given in Table 3.

TABLE 3

|  | Control (%) | Treated with Anti-IFN-$\alpha/\beta$ | Treated with Anti-IFN-$\gamma$ |
| --- | --- | --- | --- |
| Untreated control | 85 | — | — |
| IFN standard item | 41 | 37.5 | 80.5 |
|  | (51.8) | (55.9) | (5.3) |
| Untreated control | 112 | — | — |
| IFN standard item | 42.5 | 41 | 107 |
|  | (62.1) | (63.4) | (4.5) |

The numerical values in the table represent the number of plaques, showing average from 2 plates. The values in ( ) show antibody treatment to the VSV plaque number on the untreated control FL monolayer cultured cells or VSV plaque decreasing ratio (%) on FL mono-layer cultured cells, which were treated with untreated IFN standard item.

The results of the above experiment reveal that the crude extraction standard item from seeds of *Aeginetia indica* possesses IFN-$\gamma$ inducing potency.

Figure 9:
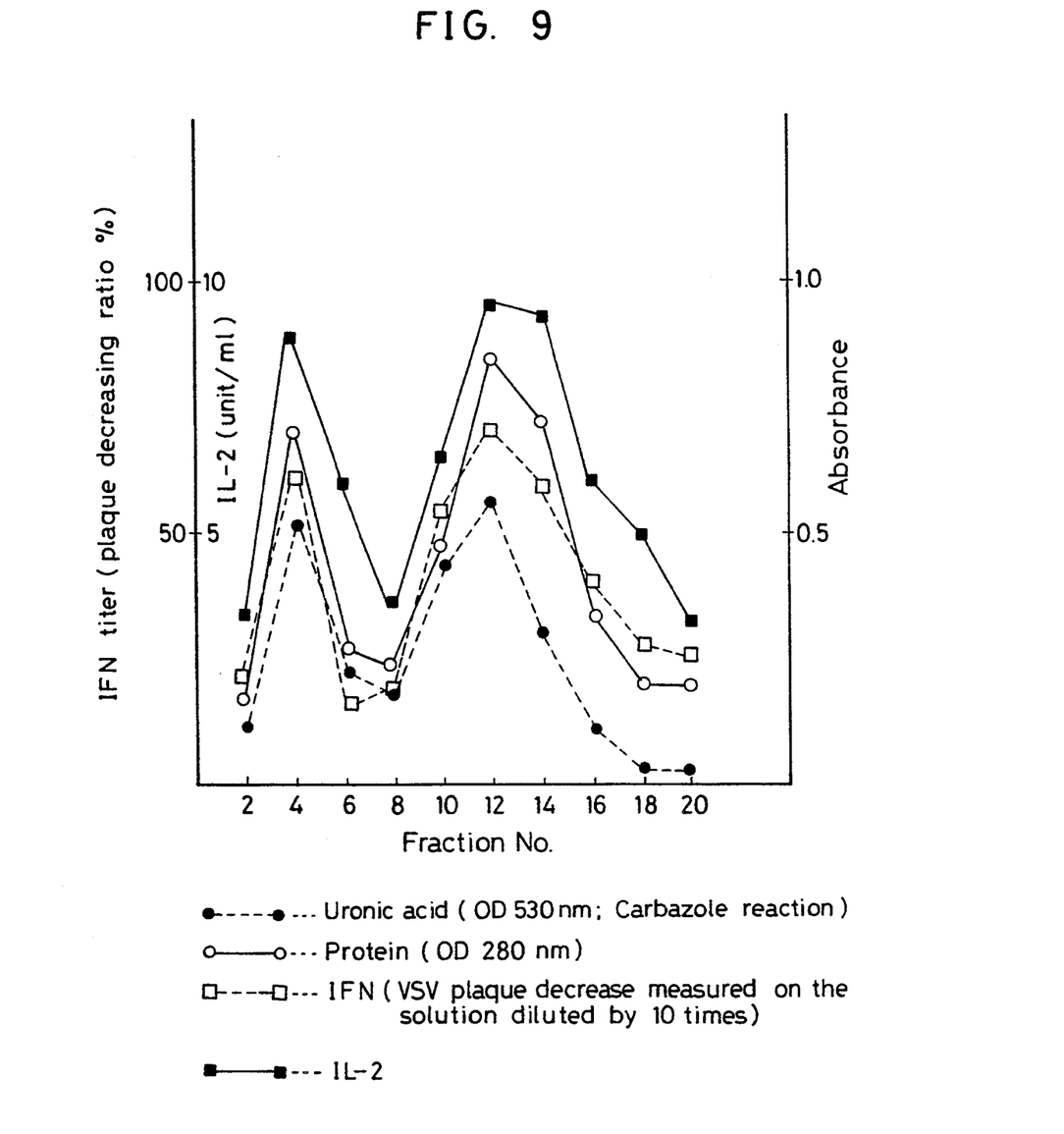

The crude extraction standard item of seeds of *Aeginetia indica* was processed through the above chromatography. For each fraction, IL-2 and IFN inducing potency was examined, and uronic acid (OD 530 nm; carbazole reaction) and protein (ODD 280 nm) were determined. The results are shown in FIG. 9. In this measurement, IFN titer shows VSV plaque decreasing ratio (%) for the solution diluted by 5 times.

As it is evident from FIG. 9, IL-2 and IFN inducing potency, quantity of uronic acid and protein showed the same trend in all fractions, and this reveals that the crude extracts of the present invention are a single substance.

Then, using 500 $\mu$g each of the fractions (determined by uronic acid quantitative analysis) prepared in the extraction examples 2 and 3 from seeds of *Aeginetia*

*indica*, PBMC was stimulated for 24 hours, and IL-2 titer of the supernatant was measured. PBMC was prepared from 6 subjects of A, B, C, D, E and F. Table 4 summarizes the results of the measurement of IL-2 titer. (Unit: unit/ml)

TABLE 4

| PBMC samples | Extraction example 2 | Extraction example 3 |
|---|---|---|
| A | 12.5 | 3.2 |
| B | 11.2 | 2.5 |
| C | 15.3 | 4.3 |
| D | 16.2 | 5.5 |
| E | 18.3 | 6.6 |
| F | 13.6 | 3.8 |

As it is evident from Table 4, the extracts prepared from the extraction examples 2 and 3 have IL-2 inducing potency, while the extract from the extraction example 2 has higher IL-2 inducing potency.

Table 5 shows the results of the measurement of IFN-$\gamma$ titer of the extracts prepared in the extraction examples 2 and 3. For the measurement, PBMC was treated with the polysaccharide fractions prepared in the extraction examples 2 and 3 for 24 hours, and the supernatant was diluted by 5 times. The diluted standard items were divided to those treated with anti-IFN-$\gamma$ and those not treated. Then, VSV plaques were formed by treating FL monolayer cultured cells with the standard items. Thus, the number of VSV plaques in anti-IFN-$\gamma$ treated or untreated FL monolayer cultured cells were compared. The values show the decreasing ratio (%).

TABLE 5

| PBMC sample | Extraction example 2 Anti-IFN-$\gamma$ | | Extraction example 3 Anti-IFN-$\gamma$ | |
|---|---|---|---|---|
| | Untreated | Treated | Untreated | Treated |
| A | 68.8 | 3.8 | 52.8 | 3.2 |
| B | 63.5 | 4.1 | 48.2 | 4.8 |
| C | 79.3 | 8.9 | 68.5 | 7.8 |
| D | 85.2 | 9.1 | 71.7 | 7.9 |
| E | 87.4 | 9.5 | 78.3 | 6.5 |
| F | 69.5 | 4.2 | 55.4 | 3.7 |

As it is apparent from Table 5, those extracted in the extraction examples 2 and 3 possess high IFN-$\gamma$ inducing potency.

Figure 10:
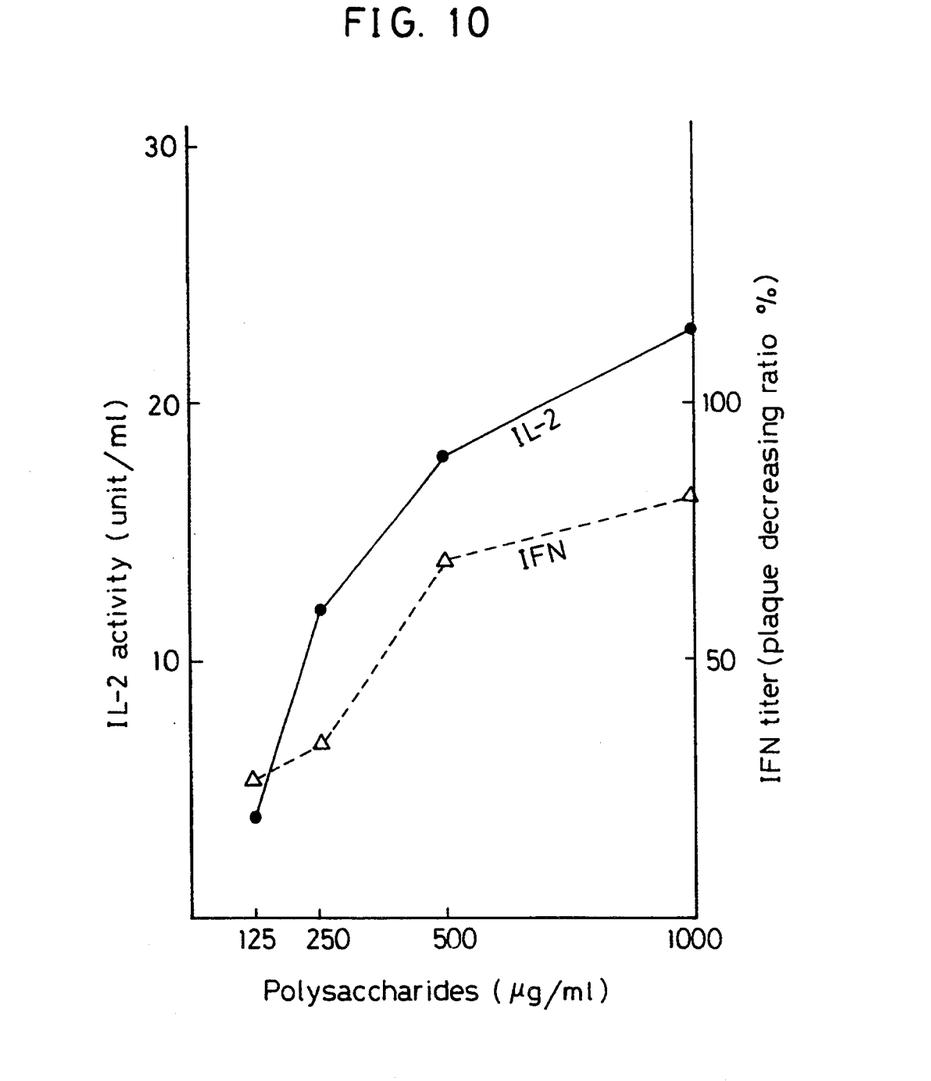

Next, PBMC was stimulated for 24 hours with polysaccharide fractions prepared in the extraction example 2, and the IL-2 and IFN titers of the supernatant were measured. The results are shown in FIG. 10. IFN titers were measured by VSV plaque decreasing ratio on the standard items obtained by diluting the PBMC supernatant by 5 times. The transition of IL-2 activity is represented by solid circles, and that of IFN titers is shown by open triangles.

From FIG. 10, it is made clear that both IL-2 and IFN titers increase in response to the quantity of polysaccharides.

When 1 mg and 3 mg of the polysaccharides (500 $\mu$g by uronic acid determination) as prepared in the extraction example 2 were injected intraperitoneally in 10 BALB/c mice, there was no abnormal sign even after 28 days.

According to the present invention, it has been found that IL-2 and IFN inducing agents extracted from each of the above extraction examples exert action as carcinostatic agents.

In the following, more concrete description will be given on the present invention.

In the following concrete examples of the invention, ddY mice were used as the animal, and Sarcoma-180 graftable to ddY mice (hereinafter referred as "S-180") was used as tumor cell. Also, in the following concrete examples, the extract obtained in the above extraction example 2 is referred as the extract 2, and that of the extraction example 3 is referred as the extract 3.

Concrete Example 1

Therapeutic effect of the extract 2 on ascites type tumor $2\times10^6$ S-180 tumor cells were grafted intraperitoneally to ddY mice, and the survival rate was studied.

Figure 1:
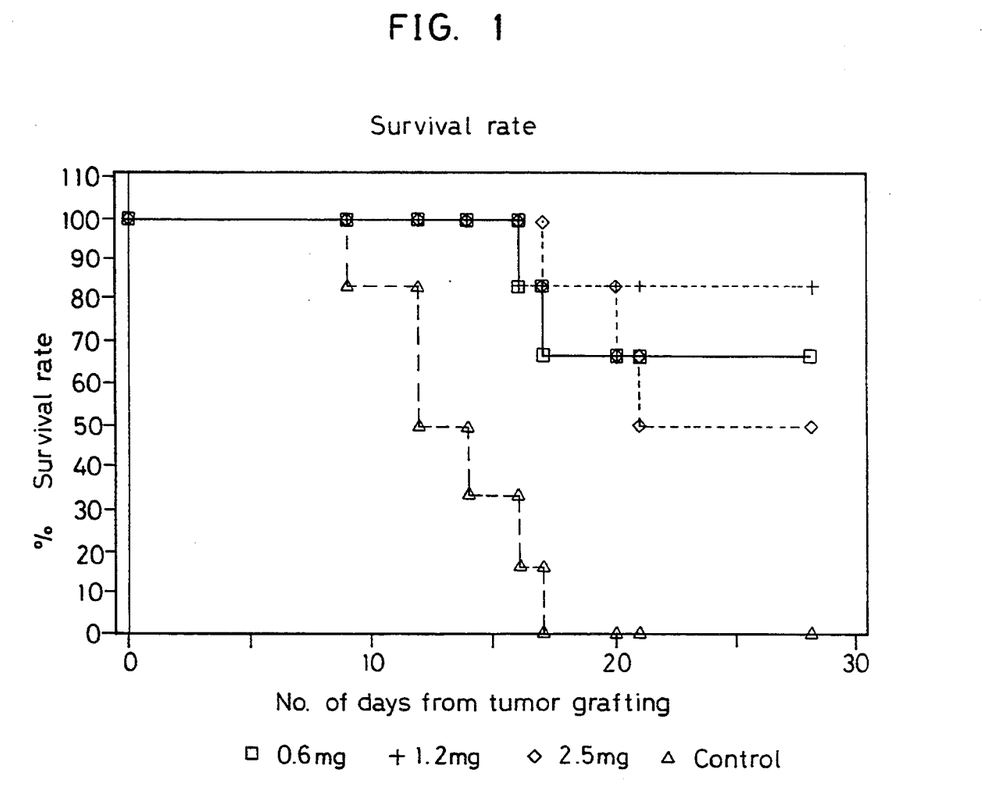
FIG. 1 is a diagram of survival rate showing therapeutic effect of the carcinostatic agent of the present invention on ascites type tumor.

As shown in FIG. 1, the mice with no administration of the extract 2 ($\Delta$) all died from tumor (6 mice) up to the day 17 after the grafting of S-180.

In contrast, in case of the mice, to which the extract 2 had been given intraperitoneally by 0.6 mg/kg ($\square$), 1.2 mg/kg (+) and 2.5 mg/kg ($\diamond$) once in every two days from the day of tumor grafting, the survival rate increased in all cases.

Specifically, 3 of 6 mice, to which the extract 2 had been given by 0.6 mg/kg survived up to the day 29 after tumor grafting. 5 of 6 mice in the 1.2 mg/kg group, and 4 of 6 mice in the 2.5 mg/kg group survived to the day 29.

Although the data are not given, there was no noticeable side effect when the extract was given to normal mice by 0.6 mg/kg–2.5 mg/kg once in every two days.

Figure 2:
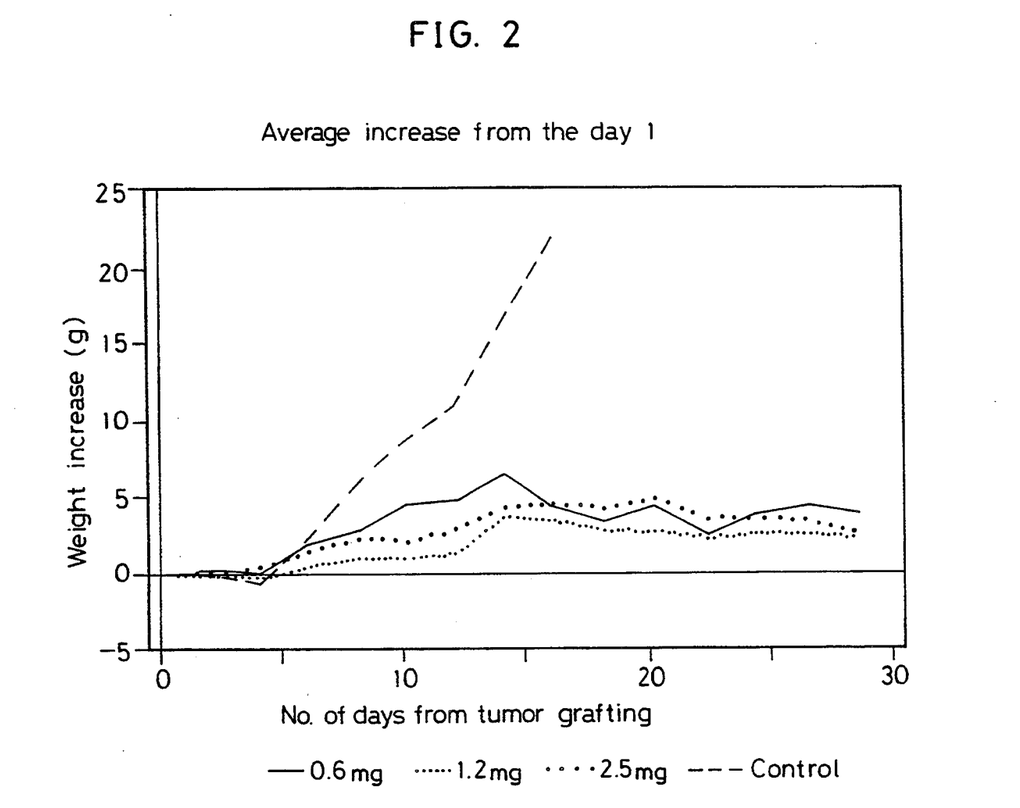
FIG. 2 exhibits proliferation of intraperitoneal tumor cells of mice with carcinoma by weight increase.

FIG. 2 shows the results of the proliferation of intraperitoneal tumor cells in the mice with carcinoma evaluated by weight increase.

The mice with carcinoma with no administration of the extract 2 (--) showed weight increase of 20 g or more after intraperitoneal grafting of the tumor. On the other hand, in the cases of the mices, to which the extract was given by 0.6 mg/kg (—), 1.2 mg/kg (----), and 2.5 mg/kg (....) and which survived up to the day 29, weight increase was less than 5 g in all cases.

Concrete Example 2

After S-180 tumor was grafted intraperitoneally, the extract 2 was given to the mice and the mice survived for long time. Then, the drug administration was suspended, and S-180 was grafted again.

To the mice, which survived for long time (29 days or more), the drug administration was discontinued, and S-180 tumor cells were grafted again intraperitoneally. The results are shown in FIG. 3 by $\square$.

As the control group, S-180 was grafted to the untreated ddY mice. This is shown by $\Delta$.

Figure 3:
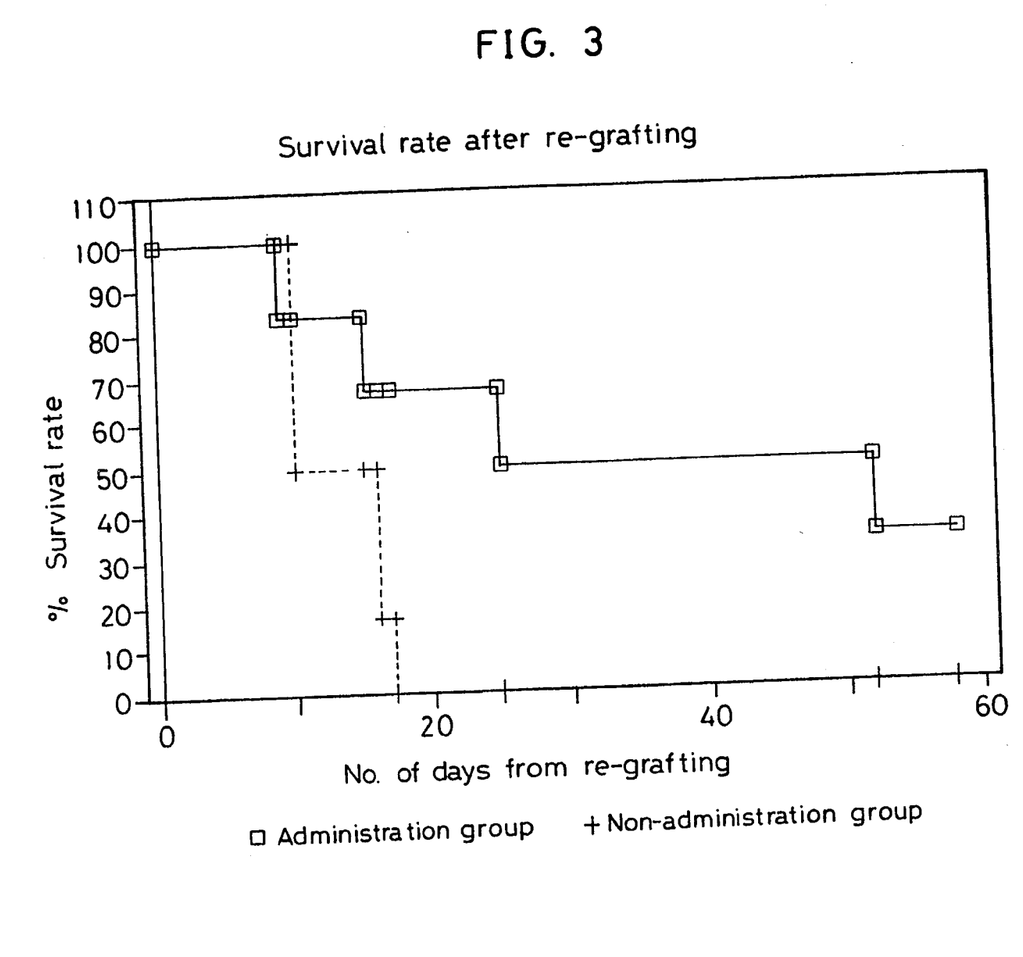
FIG. 3 is a diagram for explaining the effect of the carcinostatic agent of the present invention when it is given to mice, to which tumor had been grafted intraperitoneally and which survived for long period, and tumor was grafted again.

As it is evident from FIG. 3, the mice with long survival rate showed extremely high survival rate compared with the control group even after re-grafting.

Figure 4:
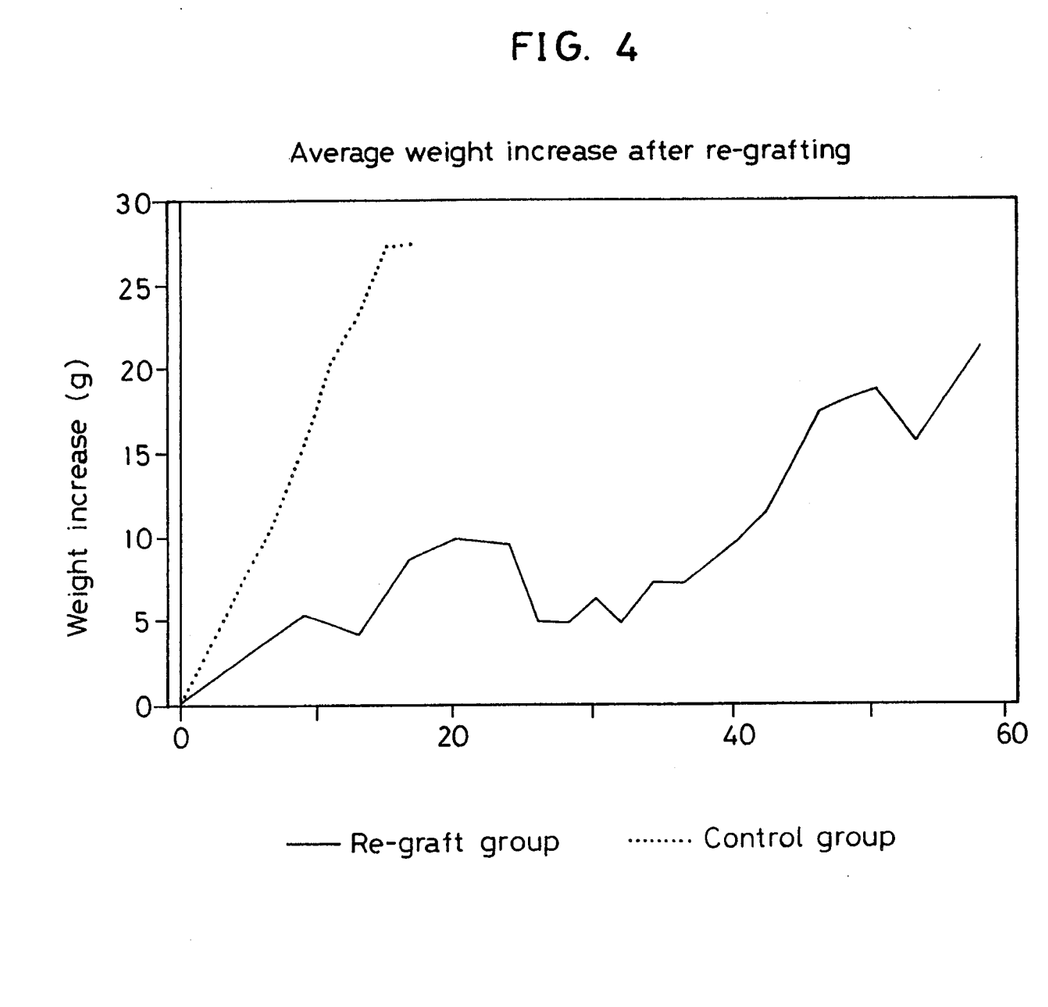
FIG. 4 shows weight changes in an experimental group of FIG. 3.

The weight changes in these experimental groups are given in FIG. 4. As it is apparent from FIG. 4, in case S-180 was grafted again to the mice with long survival (—), remarkable suppression of weight increase was noted compared with the control group (----).

Concrete Example 3

(Comparison of anti-tumor effect between the extracts 2 and 3)

After $2\times10^6$ S-180 tumor cells were grafted to ddY mice, the extract 2 and the extract 3 were given by 25 mg/kg once in every two days, and the survival ratio was evaluated. The results are given in FIG. 5.

Figure 5:
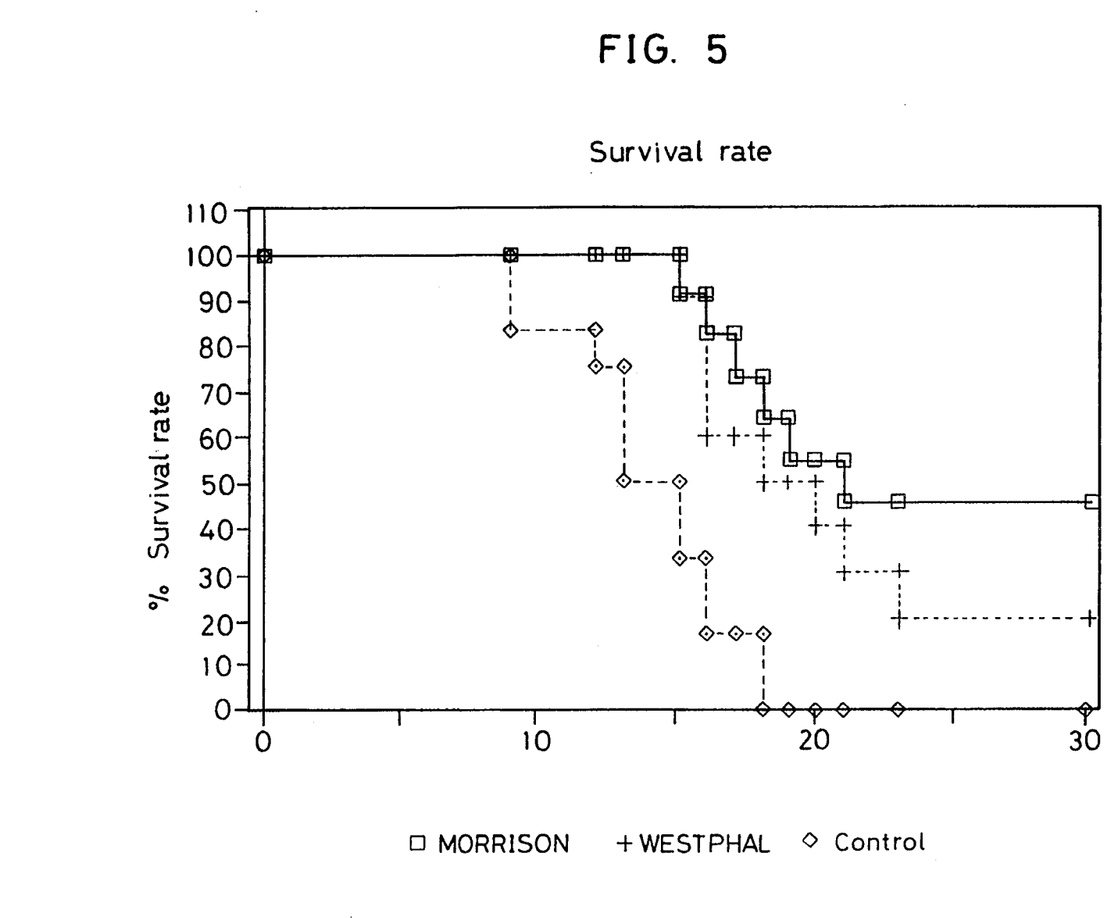
FIG. 5 shows the comparison of anti-tumor effect of an extract 2 and an extract 3, which are the carcinostatic agents according to the present invention.

As it is evident from FIG. 5, the survival ratio in the group with extract 2 (□) was slightly higher than in the group with the extract 3 (+).

Figure 6:
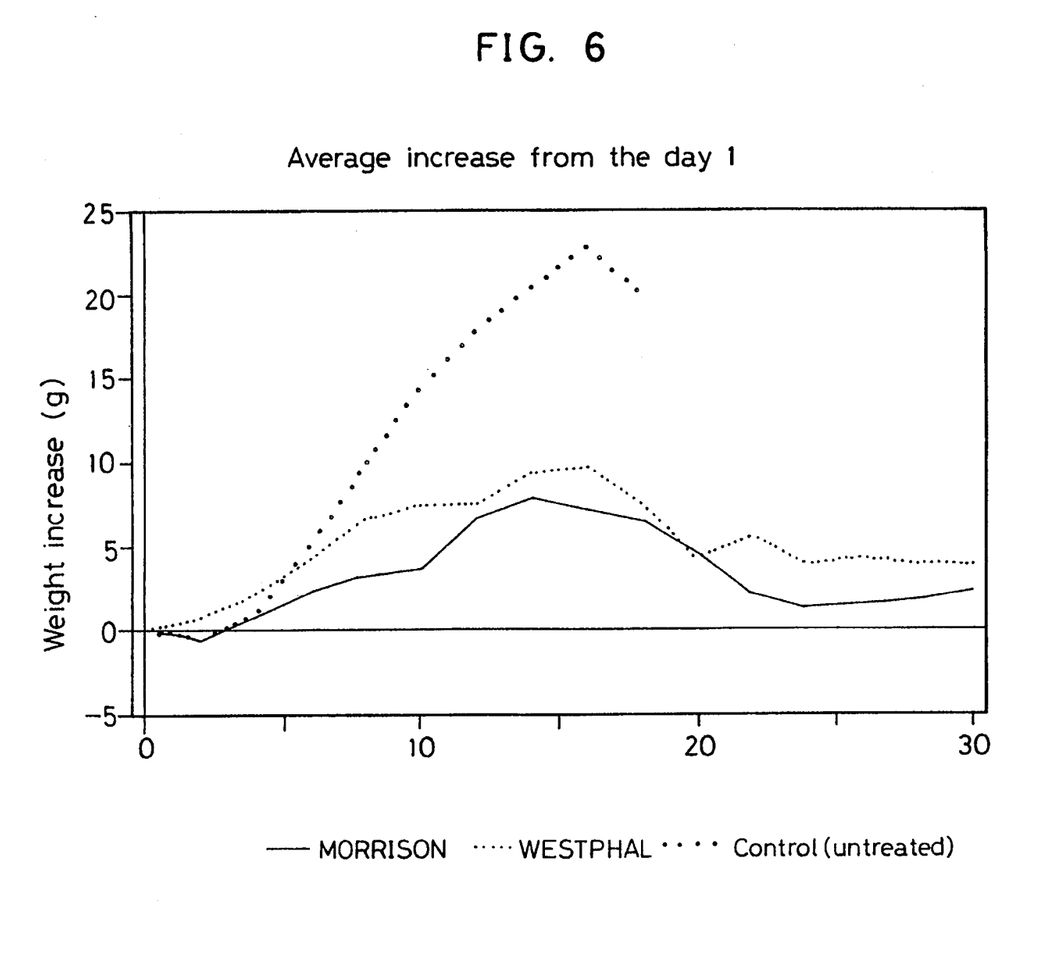
FIG. 6 shows the degree of suppressing weight increase in the mice of FIG. 5.

Next, the degree of suppression of tumor proliferation in the treated mice was observed by the degree of suppression of weight increase. The results are shown in FIG. 6.

Also in this case, the degree of suppression was slightly stronger in the extract 2 group (—) than in the extract 3 group. Both groups showed marked suppression effect when compared with the case where tumor was grafted to untreated mice (....).

Concrete Example 4

(Anti-tumor effect of the extract 2 to subcutaneously grafted tumor)

To ddY mice, $1 \times 10^6$ S-180 tumor cells were grafted subcutaneously in dorsal region, and the extract 2 was given daily into the tumor from the day 5 after grafting, and the tumor size was compared. The results are summarized in FIG. 7.

Figure 7:
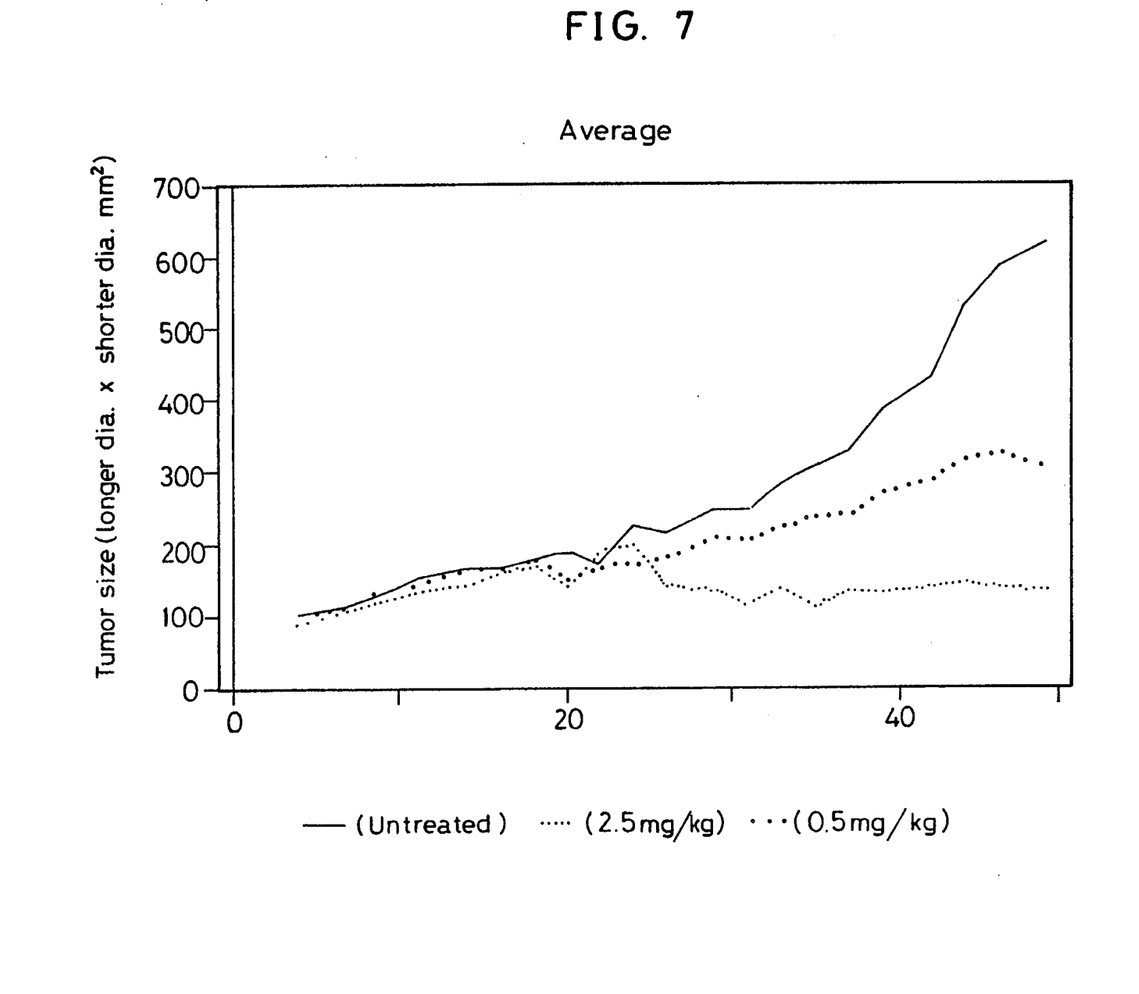
FIG. 7 is a diagram showing anti-tumor effect of the extract 2 on subcutaneously grafted tumor.

As it is evident from the figure, remarkable degree of tumor proliferation suppression was observed in both groups of 0.5 mg/kg group (....) and 2.5 mg/kg group (- - -) compared with the non-administration group (—). Particularly, tumor proliferation was almost completely suppressed in the 2.5 mg/kg group.

INDUSTRIAL APPLICABILITY

The extract from seeds of *Aeginetia indica* according to the present invention possesses interleukin-2 and interferon-γ inducing potency and is effective for the prevention and treatment of various types of virus infectious diseases in humans and animals. It has prominent tumor proliferation suppression effect and shows no noticeable side effect. Thus, it is useful as a carcinostatic agent for the treatment of the patients with carcinoma.

What is claimed is:

1. A method for suppression of tumor cell proliferation in a human or animal, comprising administering an extract of seeds of *Aeginetia indica* in distilled water to a human or animal in need of said suppression in an amount effective to suppress proliferation of said tumor cells.

2. A method for suppression of tumor cell proliferation in a human or animal, comprising administering an extract of seeds of *Aeginetia indica* to a human or animal in need of said suppression in an amount effective to suppress proliferation of said tumor cells, wherein said extract is obtained by (i) extracting said *Aeginetia indica* seeds in a water-saturated butanol mixture and obtaining the water layer of the water-saturated butanol mixture, (ii) processing the water layer with pronase, thereby precipitating protein, (iii) removing said precipitate, and (iv) ultrafiltering the resultant supernatant.

3. A method for suppression of tumor cell proliferation in a human or animal, comprising administering an extract of seeds of *Aeginetia indica* to a human or animal in need of said suppression in an amount effective to suppress proliferation of said tumor cells, wherein said extract is obtained by (i) extracting said *Aeginetia indica* seeds in a water-saturated phenol mixture and obtaining the water layer of the water-saturated phenol mixture, (ii) processing the water layer with potassium acetate and ethanol, thereby forming a precipitate, (iii) removing said precipitate and dissolving it in distilled water, dialyzing the resultant supernatant to distilled water, removing RNA from the dialysate, and condensing the dialysate.

* * * * *